US006042809A

United States Patent [19]
Tournier et al.

[11] Patent Number: 6,042,809
[45] Date of Patent: Mar. 28, 2000

[54] ADMINISTRABLE COMPOSITIONS AND METHODS FOR MAGNETIC RESONANCE IMAGING

[75] Inventors: Hervé Tournier, Valleiry, France; Michel Schneider, Troinex; Feng Yan, Carouge, both of Switzerland; Jean Brochot, Feigeres, France

[73] Assignee: Bracco Research S.A., Switzerland

[21] Appl. No.: 09/132,763

[22] Filed: Aug. 12, 1998

[30] Foreign Application Priority Data

Aug. 12, 1997 [EP] European Pat. Off. .............. 97810563

[51] Int. Cl.⁷ .................................................. A61B 5/055
[52] U.S. Cl. ......................... 424/9.3; 424/9.37; 424/9.51; 424/9.52
[58] Field of Search ..................... 424/9.3, 9.37, 424/9.52, 9.51; 600/420

[56] References Cited

U.S. PATENT DOCUMENTS

| | | | |
|---|---|---|---|
| 5,545,396 | 8/1996 | Albert et al. .............................. | 424/9.3 |
| 5,617,860 | 4/1997 | Chupp et al. ......................... | 128/653.4 |
| 5,694,934 | 12/1997 | Edelman ............................... | 128/653.4 |
| 5,785,983 | 7/1998 | Albert et al. .............................. | 424/9.3 |
| 5,789,921 | 8/1998 | Albert et al. ............................. | 324/300 |
| 5,922,304 | 7/1999 | Unger ....................................... | 424/9.3 |

FOREIGN PATENT DOCUMENTS

97/29783  8/1997  WIPO.
97/37239  10/1997  WIPO.

OTHER PUBLICATIONS

Song, Y et al., *Journal of Magnetic Resonance series A* 115(1):127–130 (1995).
Chawla, M.S., Proc. ISMRM 5th Scientific Meeting (1997) p. 2114.

Primary Examiner—Gary E. Hollinden
Attorney, Agent, or Firm—Nixon & Vanderhye

[57] ABSTRACT

The invention relates to the application of hyperpolarized gases to magnetic resonance imaging (MRI) of living subjects. The invention also concerns administrable compositions, formulations, methods of making the compositions and formulations and contrast agents involving hyperpolarized gases, as well as their use in MRI.

28 Claims, 1 Drawing Sheet

6,042,809

ADMINISTRABLE COMPOSITIONS AND METHODS FOR MAGNETIC RESONANCE IMAGING

TECHNICAL FIELD

The present invention addresses the application of hyperpolarized gases to magnetic resonance imaging (MRI). MRI is a screen display technique particularly useful for diagnosing conditions in living subjects. The invention also concerns administrable compositions, formulations, and contrast agents involving hyperpolarized gases, as well as their use in MRI.

BACKGROUND ART

In the techniques of nuclear magnetic resonance (NMR), a magnetic field acts on the nuclei of atoms with fractional spin quantum numbers and polarizes them into alignment within some selected orientations. During measurements, radio-frequency pulses of given resonance energy are applied that flip the nuclear spins and disturb the orientation distribution; then the nuclei returns (relax) to the initial state in a time dependent exponential fashion, thus giving signals which are electronically processed into recordable data. When the signals are spacially differentiated and of sufficient level, the data can be organized and displayed as images on a screen. For instance, computing the signals generated by the protons ($^1H$) of the water in contact with organic tissues enables to construct images (MRI) allowing direct visualization of internal organs in living beings. This is therefore a powerful tool in diagnosis, medical treatment, and surgery.

Despite the weakness of $^1H$ natural polarization ($6.8 \times 10^{-6}$), but due to relative abundance of water in organic tissues, hydrogen nuclei will provide sufficient signal to be processed into images of an organ under investigation, the contrasts therein being provided by the differences in spin relaxation for the protons in contact with different portions of said organ. Indeed, although compounds containing fluorine (spin ½) have been investigated as NMR signal generators in the detection of gases in subjects, only water protons have been regularly used until recently to produce MRI images. This is so because the abundance of other organic atoms with nuclear spin, i.e. some naturally occurring isotopes of phosphorus ($^{31}P$), carbon ($^{13}C$), sodium ($^{23}Na$), sulfur, etc., is much too low to provide workable imaging signals.

Recently, it has been proposed to use in the MRI of patients isotopes of some noble gases in hyperpolarized form, e.g. $^3He$, $^{129}Xe$, $^{131}Xe$, $^{83}Kr$, and the like. Indeed, although the signal from these isotopes in the naturally polarized state is extraordinarily weak (actually 5000 times weaker than from $^1H$), hyperpolarization will effectively raise it about $10^4$ to $10^5$ times. Furthermore, the spin relaxation parameters of the hyperpolarized gases are very strongly influenced by the nature of the environment in which they distribute after administration (i.e. they provide a detailed array of signals of different intensities), which makes them very interesting contrast agents in MR imaging.

Hyperpolarizing noble gases is usually achieved by spin-exchange interactions with optically excited alkali metals in the presence or in the absence of an externally applied magnetic field (see for instance G. D. Cates et al., Phys. Rev. A 45 (1992), 4631; M. A. Bouchiat et al. Phys. Rev. Lett. 5 (1960), 373; X. Zeng et al., Phys. Rev. A 31 (1985), 260). With such techniques, polarization of 90% or more is possible, the normal relaxations ($T_1$, $T_2$) being so long (from several minutes to days in the case of Xe ice) that subsequent manipulations (use for diagnostic purposes) are quite possible. Otherwise, hyperpolarization can be achieved by metastability exchange, for instance by exciting $^3He$ to the $2^3S_1$ state by radio pulses, optically pumping with 1.08 μm circularly polarized laser light to the $2^3P$ metastable state and transferring polarization to the ground state by metastability exchange collisions with the ground state atoms (see L. D. Schaerer, Phys. Lett. 180 (1969), 83; F. Laloe et al., AIP Conf. Proc. #131 (Workshop on Polarized 3He Beams and Targets, 1984).

WO 95/27438 discloses use of hyperpolarized gases in diagnostic MRI. For instance, after having been externally hyperpolarized, the gases can be administered to living subjects in gaseous or liquid form, either alone or in combination with inert or active components. Administration can be effected by inhalation or direct intravenous injection of blood which is extracorporally contacted with the gas and reintroducing the contacted blood into the body. Upon administration, the distribution of the gas within the space of interest in the subject is determined by NMR, and a computed visual representation of said distribution is displayed by usual means. No practical example of administration of a parental contrast agent composition or formulation, nor identification of the additional components is provided.

U.S. Pat. No. 4,586,511 discloses administering organic fluorinated compounds to living subjects and effecting NMR measurements including chemical shifts, relaxation times, or spin-spin couplings. MRI is not mentioned.

In an article by H. Middleton et al., Mag. Res. Med. 33 (1995), 271, there is disclosed introducing polarized $^3He$ into the lungs of dead guinea-pigs and thereafter producing an MR image of said lungs.

P. Bachert and al. Mag. Res. Med. 36 (1996), 192 disclose making MR images of the lungs of human patients after the latter inhaled hyperpolarized $^3He$.

M. S. Chawla et al. (Abstract of the Meeting on MRI Techniques Vancouver 1997) suggested using $^3He$ microbubble suspensions in an aqueous saline carrier for MR vascular imaging. To stabilize the bubbles against buoyancy, Chawla et al. recommended to incorporate 40% PEG (Mw 3,350) to the carrier liquid. The bubbles were generated by injecting the gas with a syringe into the liquid via a three-way stopcock. MRI measurements were effected in vitro; no in vivo experiments are reported.

Although the suggestion of Chawla et al. is of interest, due to considerable bubble instability it could not be considered for practical applications. Despite using bubble stabilizers recommended by Chawla et al., suspensions in a carrier liquid of microbubbles of rare gases prepared according to the suggestion by authors collapsed in a matter of seconds under no or moderate external pressure. The fact that Chawla et al. microbubbles are so unstable makes them useless from the practical point and of no interest for use in vivo, i.e. for diagnostic applications in patients.

SUMMARY OF THE INVENTION

Figure 1:
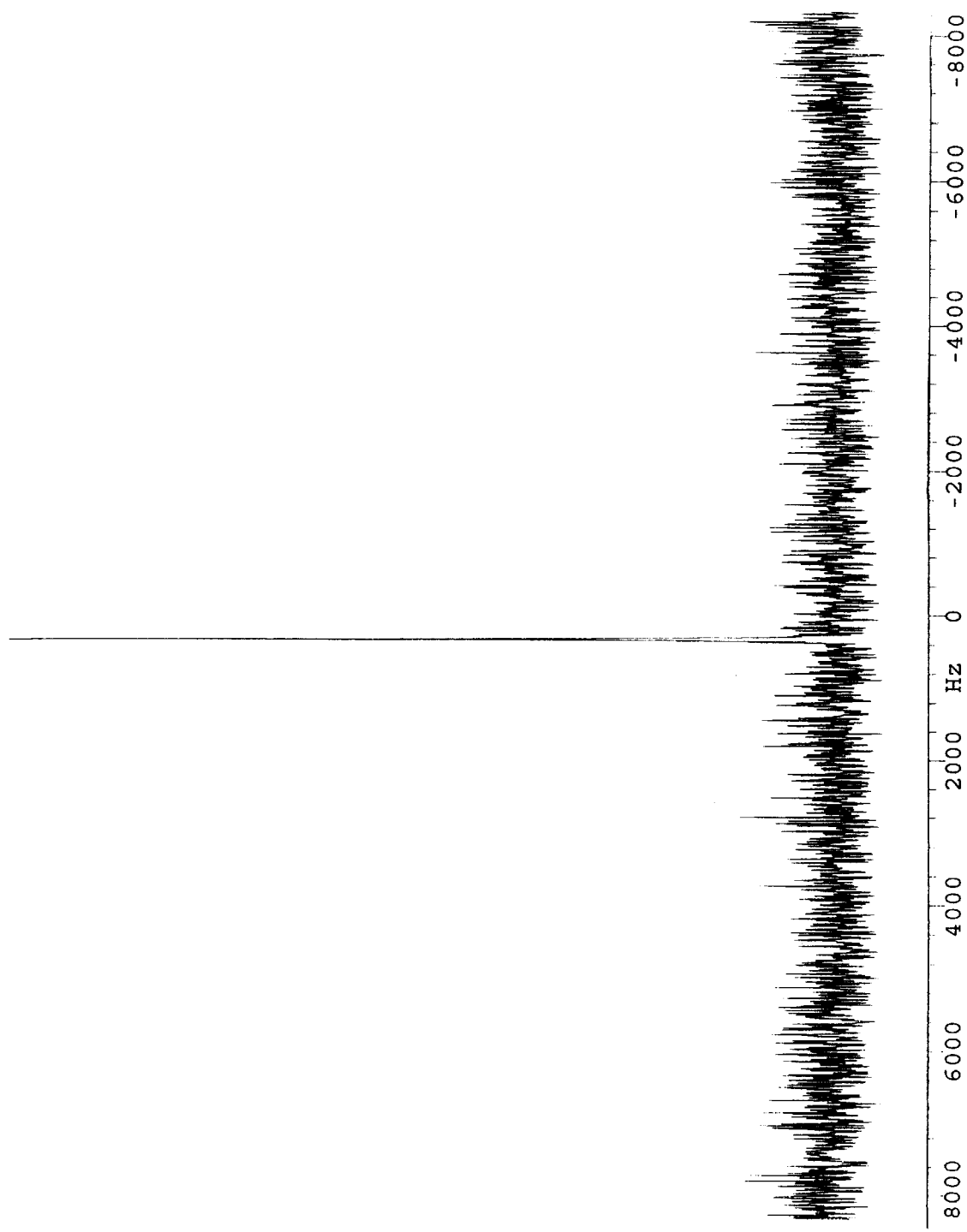
FIG. 1 is the NMR spectrum of the contrast agent of Example 3.

In a main embodiment of the invention there are disclosed injectable MRI contrast compositions or formulations in the form of dispersions or suspensions of hyperpolarized gas microvesicles in a pharmaceutically administrable carrier liquid for practical in vivo vascular and tissue MR visualization. They are based on the unexpected finding that the addition of a small proportion of some high Mw foreign inert gases, e.g. volatile fluorinated compounds such as fluorocarbons, to the hyperpolarized gases trapped in vesicles (microbubbles or microballoons) has a profound stabilizing effect. For instance, a proportion as low as 1–10% (vol) of fluorocarbons such as $C_nF_{(2n+2)}$ [n being advantageously 1–12] in microbubbles of $^3$He or $^{129}$Xe stabilized at the gas/liquid interface by amphiphilic compounds, e.g. by a phospholipid monolayer boundary (see for instance, EP-A-0 474 833 and EP-A-0 554 213), will increase considerably the stability of the bubbles under pressure.

Similarly, in a variant, instead of the foregoing microbubbles, the compositions according to the invention comprise suspensions or dispersions in a carrier liquid of microballoons filled with hyperpolarized gases and a proportion of stabilizing gas or gases. The microballoons are vesicles with a tangible material envelope, for instance of polymer as disclosed in EP-A-0 458 745.

Another object of the invention is to disclose the techniques for preparing the foregoing formulations starting with solutions of surfactant stabilizers and amphiphiles and bubbling therein mixtures of hyperpolarized gases and a proportion of stabilizing gas or gases; or otherwise, exposing powders of dessicated amphiphiles and/or surfactants to hyperpolarized gases containing a proportion of stabilizing gas or gases, and thereafter dispersing the exposed powders in an administrable carrier liquid. The noble gases are available commercially in highly purified form and the polarizable isotopes are enriched by usual means known in the art. Hyperpolarization can be effected as suggested in WO 96/39912, for instance by electron-nucleus spin exchange with optically excited rubidium vapor (G.D. Cates et al., *Phys. Rev. A* 45 (1992), 4631; M. A. Bouchiat et al. *Phys. Rev. Lett.* 5 (1960), 373; X. Zeng et al., *Phys. Rev. A* 31 (1985), 260).

In an other variant, the foregoing techniques involve preparing suspensions of microballoons filled with hyperpolarized gases containing a proportion of stabilizing gas or gases, this being achieved using emulsions of substances capable to polymerize, and under conditions where microballoons of polymer will form and entrap the said hyperpolarized gases containing a proportion of stabilizing gas or gases.

Another object of the present invention is to disclose kits comprising the components required to in situ produce the foregoing administrable compositions containing hyperpolarized gases with a proportion of stabilizing gas or gases, as well as their use for administration to subjects and subsequent imaging using usual MRI procedures.

DETAILED DESCRIPTION OF THE INVENTION

This invention is based on the unexpected finding that there can be provided administrable NMR contrast compositions or formulations comprising vesicles (microbubbles or microballoons) filled with a mixture of at least one noble gas in the hyperpolarized state and one or more inert gases. The hyperpolartized gas is defined as gas component A (major component) and the inert gas is defined as gas component B. Gas B has a relatively high Mw, i.e. >80 Daltons. The purpose of gas B is to protect the mixture by stabilizing the presence of the rare gas A within the vesicles, or in other terms to prevent collapse or coalescence thereof, or the escape of said noble gases through the vesicle envelope, the vesicles being in suspension in a carrier liquid with usual surfactants, additives and stabilisers. Formulations can be obtained that combine desirable resistance to pressure and predetermined life-time in the circulation, both of these parameters being controllable at will. As long as component B is present in certain minimal proportions and as far as its solubility in water is below 0.0283 ml of gas per ml of water under standard conditions, the MRI contrast compositions will provide diagnostically useful images in vivo and in vitro, for instance of the circulation and nearby organs. After the imaging composition has been administered to a subject, images are generated using MRI equipment as usual. It is not known yet whether the useful MR imaging signals are generated mainly by the portion of the hyperpolarized gas still encapsulated in the vesicles, or that having diffused therefrom after a time.

The quantity of component B in the contrast medium vary in most cases from as low as 0.5 volume percent (for substances with the higher molecular weights and low solubility in water) to about 30–40% (by volume). Practically, the protective effect of gas B levels off for mixtures in the higher portion of the concentrations range, i.e. it is usually of no interest to further increase the proportion of B in the mixture once the desired degree of protection has been reached. In this regard it is of interest to note that the effect of component B on the physical properties of mixture of A and B, particularly in terms of inhibition against evanescence and resistance to pressure variations, is nearly the same as if B were taken alone (i.e. in pure form). Notwithstanding, it is of interest to keep the proportion of B in the lowest range compatible with adequate microvesicle stability, this being in order to benefit from the highest possible concentration of hyperpolarized gas to generate the imaging signal. It is particularly surprising that the relaxation parameters of the hyperpolarized gases trapped within the vesicles (which constitute the key factors in the generation of useful MR images) are not significantly impeded by the presence of the stabilizing gas, nor by the substances at the surrounding gas/liquid interface. Indeed, the presence of a fluorinated gas in admixture with the hyperpolarized gas probably has the effect of decreasing the possible loss of polarization of the latter during manipulations.

Experiments have shown that substances with molecular weights below 80 are not suitable as "protective" components in the present gas mixtures; moreover the high Mw limit for B is difficult to ascertain, as most compounds tested were effective protectors as long as their molecular weight was above 80. Thus compounds with molecular weight of about 240 daltons, such as decafluorobutane, or 290 daltons such as perfluoropentane, have been found very effective "protector" components. The "major" component A correspondingly present in an amount of 60 to 99.5% by volume is a hyperpolarized gas such as $^3$He, $^{129}$Xe, $^{131}$Xe, $^{83}$Kr, or similar. These hyperpolarized gases are available according to the prior art methods. Optionally A can consist of one or more hyperpolarized rare gases in admixture with a proportion of "ordinary" gases such as oxygen, air, nitrogen, carbon dioxide or mixtures thereof. However, for component A, other less common gases in non-hyperpolarized form like argon, xenon, krypton, $CHClF_2$ or nitrous oxide may also be considered.

It was quite unexpected to find that suspending in an aqueous carrier microvesicles of a mixture formed of as little as 0.5% by volume of a substance such as dodecafluoropentane, or 0.8% by volume of decafluorobutane in admixture with noble gases, particularly $^3$He which is highly evanescent, will produce microvesicles having excellent stability and resistance to pressure variations preventing escape of the helium without detriment to the polarisation relaxivities.

It has been shown that rapid elimination of He from microbubbles is due to its low Mw which enables the gas to readily permeate external boundary media. In the case of polarized $^{129}$Xe, the bubble evanescence is due to its high solubility in aqueous carriers. Although evanescence with microbubbles may be reduced by various surfactants, additives and stabilisers, microvesicles with a material wall (microballoons) are also proposed in the present invention. Microvesicles with walls made from natural or synthetic polymers such as lipid bilayers (liposomes) or denaturated proteins like albumin in the absence or the presence of further additives are envisaged. The poor resistance to pressure variations noted in the past for microbubbles in general and the consequent loss of bubble count, inspired a search for gaseous particles with greater resistance to the pressure variations occuring in the blood stream. Although the presence of a resilient boundary material has proved beneficial regarding microvesicle stability under pressure, the incorporation therein of a portion of stabiliser gases such as sulfur hexafluoride or dodecafluoropentane will still improve durability. Experimentation with these gases have indicated that upon injection, the suspensions of microbubbles or microballoons filled with these gases in low proportion admixtures with hyperpolarised gases are indeed very resistant to collapse in the circulation. As a result of these initial findings, close to 200 different gases have been identified as potentially useful for stabilizing MRI contrast agents containing hyperpolarized gases. It has thus been unexpectedly found that by mixing relatively small proportions of some of these gases with the hyperpolarized noble gases, microvesicles resistant to pressure may be obtained. These microvesicles will have acceptable physiological tolerance, and appropriate resorption half-life in the blood, adequate MRI signal generation properties and the good pressure resistance due to the presence of the protective gases. It is postulated that this surprising behaviour of the gas mixtures of the present invention arises because diffusion of the highly evanescent component A into the surrounding media is slowed by the presence of the large gaseous molecules of component B. Although the reasons for this surprising behaviour are yet unexplained, it can be postulated that the molecules of component B, even though in very minor amount, do actually "plug the holes" in the microbubble or microballoon boundary and thus prevent escape of the low molecular weight $^3$He, or very soluble $^{129}$Xe, by transmembrane diffusion.

The preferred gases to be used as component B in the present compositions and formulations are substances which may be gaseous or liquid at room temperature but which will instantly volatilize at body temperature. One may cite the following substances: sulfur hexafluoride, tetrafluoromethane, chlorotrifluoromethane, dichlorodifluoromethane, bromotrifluoromethane, bromochlorodifluoromethane, dibromodifluoromethane dichlorotetrafluoroethane, chloropentafluoroethane, hexafluoroethane, hexafluoropropylene, octafluoropropane, hexafluorobutadiene, octafluoro-2-butene, octafluorocyclobutane, decafluorobutane, perfluorocyclopentane, dodecafluoropentane and more preferably octafluorocyclobutane, octafluoropropane and decafluorobutane. The formulations in this invention preferably contains as gas B a gas selected from tetrafluoromethane, hexafluoroethane, hexafluoropropene, octafluoropropane, hexafluoro-butadiene, octafluoro-2-butene, octafluorocyclobutane, decafluorobutane, perfluorocyclopentane, dodecaflu-oropentane and more preferably sulfur hexafluoride and/or octafluorocyclobutane.

When filled with the contrast gas mixture of the invention and dispersed in an aqueous carrier containing usual surfactants, additives and stabilisers, the microbubbles formed provide a useful MRI contrast composition. In addition to the microbubbles, the contrast composition of the invention will contain surfactants, additives and stabilizers. Surfactants which may include one or more film forming surfactants in lamellar or laminar form are used to stabilize the microbubble evanescent gas/liquid boundary. Hydrating agents and/or hydrophilic stabilizer compounds such as polyethylene glycol, carbohydrates such as lactose or sucrose, dextran, starch, and other polysaccharides, or other conventional additives like polyoxypropylene glycol and polyoxyethylene glycol; ethers of fatty alcohols with polyoxyalkylene glycols; fatty acids and esters of fatty acids with polyoxyalkylated sorbitan; soaps; glycerol-polyalkylene stearate; glycerolpolyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyakylated; mono-, di- and triglycerides of saturated or unsaturated fatty acids; glycerides of soya-oil with sucrose may also be used. Surfactants may be film forming and non-film forming and may include polymerizable amphiphilic compounds of the type of linoleyl-lecithins or polyethylene dodecanoate. Among non-film forming surfactants one may use block copolymers of polyoxypropylene and polyoxy ethylene. Preferably, the surfactants are film forming and more preferably are phospholipids selected from phosphatidic acid, phosphatidylcholine, phosphatidylethanolamine, phosphatidylserine, phosphatidylglycerol phosphatidylinositol, cardiolipin, sphingomyelin and mixtures thereof.

It has been mentioned that the invention is not limited to contrast formulation consisting of suspensions of microbubbles as vehicles for the magnetized rare gases used in this invention. Any suitable hollow bead-like particle filled with the contrast gaseous mixtures e.g. liposomes or microballoons having an envelope produced from synthetic or natural polymers or proteins may conveniently be used. Thus it has been established that microballoons prepared with albumin, or liposome vesicles or iodipamide ethyl ester porous particles when filled with the gasous contrast mixtures of the invention, provide good imaging agents. Suspensions in which the microbubbles were stabilised with sorbitol or non-ionic surfactants such as polyoxyethylene/polyoxypropylene copolymers (commercially known as Pluronic®) have demonstrated equally good imaging capability when compared to that of the original formulations made with the pure hyperpolarized gases taken alone. It is therefore, believed that the invention offers a more generalised concept of MRI contrast media and offers better control of contrast agent properties. The media and contrast agents containing the media of the invention are, therefore, considered as products which take the MRI technique one step further in its development.

The invention also comprises a method of making the present MRI contrast formulations, in which a gas mixture of at least two components A and B is suspended in a physiologically acceptable aqueous carrier liquid containing usual surfactants and stabilisers so as to form gas filled microbubbles or microballoons. This method is characterised in that the minimum effective proportion of component (B) in said mixture of gases is determined according to the relation:

$$B_c\% = K/e^{b \, M_{wt}} + C$$

in which $B_c\%$ (by vol.) is the total quantity of the component B in the mixture, K & C are constants with values of 140 and −10.8 respectively, $M_{wt}$ represents the molecular weight of component B exceeding 80 and b is a complex function of operating temperature and thickness of the membrane (a lipid film) that stabilizes the microbubbles; however, since the body temperature is substantially constant and the stabilizer film structure substantially independent of lipid concentration, the value of b keeps in the interval 0.011–0.012, and it may be considered a constant. The contrast agents made according to the method comprise suspensions of microbubbles or microballoons with excellent resistance to pressure variations and a relatively rapid resorption. Both of the properties are controlled to the extent that practically custom-tailored MRI agents are now possible. With the above criteria it is possible to produce an agent with desired characteristics starting from any available non-toxic ("of the shelf") substance which at body temperature is gas and which has the molecular weight and solubility in water as explained above. The manipulations required for making the present formulations are detailed in documents EP-A-0 474 833, EP-A-0 554 213 and EP-A-0 458 745.

For instance, examples of preparation of microballoons to be advantageously used within the scope of this invention involve making an oil-in-water emulsion into droplets of a polymer organic solution in an aqueous phase carrier, causing the polymer to deposit at the droplet to carrier interface (for instance interfacial precipitation by dilution) to provide water or solvent-filled microvesicles in suspension in the carrier, and eventually subjecting the suspension to conditions (e.g. freeze-drying) whereby the solvent trapped within the vesicles will evaporate and be replaced by the gas mixture of the invention. Polymers that will qualify for the above method include biodegradable polymer selected from polysaccharides, polyamino-acids, polylactides and polyglycolides and their copolymers, copolymers of lactides and lactones, polypeptides, poly-(ortho)esters, polydioxanone, poly-β-aminoketones, polyphosphazenes, polyanhydrides and poly(alkylcyanoacrylates). More specifically, one may cite polyglutamic or polyaspartic acid derivatives and their copolymers with other amino-acids. Additives may also be incorporated as blends with the polymers, such as plasticizers like isopropyl myristate, glyceryl monostearate and the like to control flexibility, amphipatic substances such as surfactants and phospholipids like the lecithins to control permeability by increasing porosity and hydrophobic compounds such as high molecular weight hydrocarbon like the paraffin-waxes to reduce porosity.

Alternatively, the polymers may contain fluorine atoms as disclosed in WO96/04018, namely by covalently binding with a F-containing compound such as perfluoromethyl and perfluoro-t.butyl moieties. Otherwise, introduction of fluorinated moieties can be brought about by reaction with perfluorinated gases such as perfluoropropane, perfluorinated alkyl esters and perfluorinated acyl halides and anhydrides.

Additional polymers are also convenient for the microballoons of the invention, namely fluorinated and/or deuterated polysiloxanes and polysilanes as disclosed in WO96/39912.

The invention also includes a dry formulation comprising surfactants, additives and stabilisers stored under a gasous mixture comprising one or more hyperpolarized gases (gaseous component A) and one or more protective gases (gaseous component B). The dry formulation comprises lyophilised film forming surfactants and, optionally, hydrating agents like polyethylene glycol or other conventional hydrophilic substances. Prior to injection, the dry formulation is admixed with a physiologically acceptable carrier liquid to produce the MRI contrast composition of the invention. The film forming surfactant is, preferably, a phospholipid selected from phosphatidic acid, phosphatidylcholine, phosphatidylethanolamine, phosphatidylserine, phosphatidylglycerol phosphatidylinositol, cardiolipin, sphingomyelin and mixtures thereof.

In a variant, stabilisation of the microbubble evanescent gas/liquid envelope may be secured by non-ionic surfactants such as copolymers of polyoxyethylene and polyoxypropylene in combination with a film forming surfactant such as dipalmitoylphosphatidylglycerol. As before the aqueous liquid carrier may further contain hydrophilic additives such as glycerol, PEG, sorbitol, etc. Furthermore, useful agents of the invention may be prepared with saline solutions containing Tween® 20, sorbitol, soybean oil, and optionally other additives.

Also proposed is a two-component kit comprising as a first component a dry formulation of surfactants, additives and stabilisers stored under a mixture of gases and as a second component a physiologically acceptable carrier liquid which when brought into contact with the first component provides an MRI contrast formulation. The kit may include a system of two separate vials, each containing one of the components, which are interconnected so that the components may be conveniently brought together prior to use of the contrast agent. Clearly, the vial containing the dry formulation will at the same time contain the gaseous mixture of components A and B according to the invention. Conveniently, the kit may be in the form of a prefilled two compartment syringe and may further include means for connecting a needle on one of its ends.

Also proposed is a three-component kit comprising a first component as a dry formulation of surfactants, additives and stabilisers stored under partial pressure of the stabilising gas (B), a second component a hyperpolarized gas (A) and a third component physiologically acceptable carrier liquid.

The invention further comprises a method of making contrast formulations with microbubbles containing the MRI contrast gasous mixture of A and B, as well as their use in imaging of organs in human or animal patients.

When used for imaging of organs in human or animal body the MRI contrast medium of the invention is administered to the patient in the form of a microvesicle aqueous suspension in the above described physiologically acceptable carrier liquid and the patient is scanned with an MRI apparatus whereby an image of the organ or the part of the body imaged is produced.

The following examples further illustrate the invention:

EXAMPLE 1

Fifty eight milligrams of diarachidoylphosphatidylcholine (DAPC), 2.4 mg of dipalmitoylphosphatidic acid (DPPA) both from Avanti Polar Lipids (USA) and 3.94 g of polyethyleneglycol (PEG 4000 from Siegfried, CH) were dissolved at 60° C. in tert-butanol (20 ml). The clear solution was rapidly cooled at −45° C. and freeze-dried to a white solid. Aliquots (25 mg) of said white solid were introduced in 10 ml glass vials.

The vials were closed with rubber and evacuated under vacuum. Thereafter, mixtures of xenon with various amounts of fluorocarbon were introduced into the vials via a needle through the stopper.

TABLE 1

| Gas A | Gas B | Gas B % vol | Pc mmHg |
|---|---|---|---|
| Xenon | — | 0 | 50 |
| Xenon | $C_4F_8$ | 5 | 147 |
| Xenon | $C_4F_8$ | 10 | 181 |

Bubble suspensions were obtained by injecting in each vial 10 ml of a 3% glycerol solution in water followed by vigorous mixing. The resistance to pressure $P_c$ was determined using a nephelometric assay (as described in EP-A-0 554 213). The values in the Table correspond to the pressure (over atmospheric) at which about half of the bubbles originally present are destroyed. The bubble concentration and mean bubble size were determined by analysis with a Coulter Multisizer II (Coulter Electronics Ltd). The mean bubble size was 2.0 μm.

The foregoing results indicate that the resistance of the xenon bubbles to collapse is considerably increased with already 5% $C_4F_8$. Furthermore, as acertained by NMR, the polarizazion of hyperpolarized xenon samples containing the $C_4F_8$ lasted longer under storage than those with no fluorocarbon.

EXAMPLE 2

An anhydrous formulation was prepared as in Example 1, by homogenizing together the following ingredients:
  Disteraroylphosphatidylcholine (DSPC) 30 mg
  Dipalmitoylphosphatidylglycerol (DPPG) 30 mg
  Polyethylene glycol 4000 (PEG) 3.94 g
  Tert-butanol (t.BuOH) 20 ml 20 mg samples of the above blend were placed in rubber plugged vials and, after evacuation under vacuum, gases, or mixture of gases (Table 2) were introduced therein. Portions of 10 ml saline were introduced in the vials

TABLE 2

| Gas (A + % B) | Bubble count (×10⁶) 0 hrs | Bubble count (×10⁶) 6 hrs | Encaps. vol. (μl/ml) 0 hrs | Encaps. vol. (μl/ml) 6 hrs | Pc 50% mmHg 0 hrs | Pc 50% mmHg 6 hrs |
|---|---|---|---|---|---|---|
| He (+0% B) | 14.4 | — | 0.1 | — | ind | ind |
| Xe (+0% B) | 7.4 | — | 0.1 | — | ind | ind |
| He (+10% $C_4F_{10}$) | 320 | 310 | 7.4 | 8.1 | 438 | 400 |
| He (+20% $C_4F_{10}$) | 311 | 300 | 7.1 | 7.4 | 532 | 477 |
| Xe (+10% $C_4F_{10}$) | 320 | 311 | 5.6 | 5.1 | 553 | 334 |
| Xe (+20% $C_4F_{10}$) | 421 | 428 | 7.7 | 7.2 | 588 | 470 | through a needle and bubble suspensions were generated by agitation. In Table 2 below, there are indicated the gases used, the bubble count (initial and after 6 hrs), the volume (μl/ml) of encasulated gas, and the applied pressure mmHg required to cut the bubble count by two. Note that for pure He and Xe, no result exists after 6 hrs since the bubbles had all colapsed. "Ind" means that the value was too low to be determined accurately.

The above results again stress the importance of a proportion of component B to stabilize the bubbles.

EXAMPLE 3

Using the procedure of Example 2 and 20 mg aliquots were taken from a mixture of DSPC (30 mg); DPPG (30 mg); PEG (3 g), and t.BuOH (20 ml). The samples were placed into vials and exposed to various gases or mixture of gases (see Table below). Bubble suspensions were generated as in the previous Examples and tested. The results are gathered in the following Table.

TABLE 3

| Gas B (10%) | Time (Hrs) | Bubble count (×10⁶) He | Bubble count (×10⁶) Xe | Encaps. vol. (μl/ml) He | Encaps. vol. (μl/ml) Xe | Pc 50% mmHg He | Pc 50% mmHg Xe |
|---|---|---|---|---|---|---|---|
| None | t = 0 | 12.8 | 12.9 | 0.7 | 0.2 | 43.7 | ind |
|  | t = 6 | 7.1 | 9.5 | 0.1 | 0.1 | ind | ind |
| $CF_4$ | t = 0 | 216 | 143 | 4.8 | 4.7 | 115 | 131 |
|  | t = 6 | 106 | 105 | 4.1 | 3.7 | 135 | 121 |
| $C_2F_6$ | t = 0 | 262 | 201 | 6.1 | 4.6 | 320 | 330 |
|  | t = 6 | 241 | 147 | 5.8 | 3.8 | 311 | 267 |
| $C_3F_8$ | t = 0 | 249 | 272 | 6.3 | 6.2 | 383 | 399 |
|  | t = 6 | 217 | 262 | 6.8 | 5.7 | 328 | 288 |
| $C_4F_{10}$ | t = 0 | 318 | 336 | 7.4 | 5.5 | 438 | 553 |
|  | t = 6 | 310 | 343 | 8.1 | 5.1 | 400 | 335 |
| $C_5F_{12}$ | t = 0 | 313 | 360 | 7.2 | 5.4 | 429 | 434 |
|  | t = 6 | 311 | 367 | 7.3 | 5.2 | 379 | 357 |
| $C_6F_{14}$ | t = 0 | 174 | 136 | 6.0 | 7.6 | 232 | 228 |
|  | t = 6 | 190 | 123 | 6.6 | 7.0 | 231.3 | 229 |

The data of the foregoing Table again show the effect of the addition of various fluorocarbons to the noble gases on the stability of the microbubbles.

EXAMPLE 4

The manipulations of Example 3 were repeated using $C_4F_{10}$ as the protective gas B in various proportions in hyperpolarized $^3$He. The conditions and results are summarized in Table 4 below.

TABLE 4

| % $C_4F_{10}$ | Bubble count ×10⁶ at t (Hrs) 0 | Bubble count ×10⁶ at t (Hrs) 6 | Encaps. Volume (μl/ml) at t (Hrs) 0 | Encaps. Volume (μl/ml) at t (Hrs) 6 | $P_c$50% mmHg at t (Hrs) 0 | $P_c$50% mmHg at t (Hrs) 6 |
|---|---|---|---|---|---|---|
| 0 | 12.8 | 7.1 | 0.7 | 0.1 | 44 | — |
| 1 | 143 | 64.6 | 2.0 | 1.4 | 91 | 116 |
| 3 | 189 | 150 | 3.0 | 2.9 | 266 | 280 |
| 5 | 147 | 120 | 3.3 | 3.6 | 265 | 262 |
| 10 | 295 | 260 | 4.5 | 4.5 | 431 | 429 |
| 20 | 240 | 285 | 8.5 | 8.3 | 500 | 452 |

Table 5 summarizes the results when the above experiments were run with Xe.

TABLE 5

| % $C_4F_{10}$ | Bubble count ×10⁶ at t (Hrs) 0 | Bubble count ×10⁶ at t (Hrs) 6 | Encaps. Volume (μl/ml) at t (Hrs) 0 | Encaps. Volume (μl/ml) at t (Hrs) 6 | $P_c$50% mmHg at t (Hrs) 0 | $P_c$50% mmHg at t (Hrs) 6 |
|---|---|---|---|---|---|---|
| 0 | 12.9 | 9.5 | 0.2 | 0.1 | — | — |
| 1 | 153 | 94.3 | 2.0 | 1.7 | 178 | 124 |
| 3 | 170 | 133 | 3.6 | 3.0 | 265 | 170 |
| 5 | 193 | 171 | 3.8 | 3.9 | 343 | 224 |
| 10 | 284 | 278 | 5.1 | 5.0 | 436 | 323 |
| 20 | 315 | 316 | 7.2 | 6.7 | 548 | 455 |

Results in Tables 4 and 5 show that as little as 1% of decafluorobutane has already significant stabilizing effect on both hyperpolarized xenon and helium.

EXAMPLE 5

NMR spectrum of the contrast agent prepared according to Example 3 (90% of Hyperpolarised xenon and 10% of decafluorobutane) obtained with Oxford magnet at 2 Tesla is shown in FIG. 1. $^{129}$Xe showed its peak at 23.55 MHz.

We claim:

1. Gas filled microvesicles bounded by a gas/liquid interface in a liquid carrier comprising one or more amphiphiles stabilizing microvesicles or a polymeric membrane, characterized in that the gas comprises a mixture of a hyperpolarized gas and a halogenated gas.

2. The microvesicles of claim 1, wherein the hyperpolarized gas is selected from $^3$helium, argon, $^{129}$xenon, $^{131}$xenon or krypton, preferably helium or xenon.

3. The microvesicles of claim 1, wherein said halogenated gas is fluorinated, preferably perfluorinated.

4. The microvesicles of claim 3, wherein the fluorinated gas is selected from at least one of $SF_6$, $CF_4$, $C_2F_6$, $C_3F_6$, $C_3F_8$, $C_4F_6$, $C_4F_8$, $C_4F_{10}$, $C_5F_{10}$, $C_5F_{12}$, $C_6F_{14}$ and mixtures thereof.

5. The microvesicles of claim 1, having an average size of 0.1–10 μm.

6. The microvesicles of claim 1, wherein said amphiphile is selected from sugar derivatives, natural or synthetic amphiphilic polymers, polyoyxethylene-polyoxypropylene block copolymers, phospholipids and the like.

7. The microvesicles of claim 6, wherein said phospholipids comprises hydrophilic moieties selected from the group consisting of choline, ethanolamine, serine, glycerol, pentoses and hexoses.

8. The microvesicles of claim 6, wherein the phospholipid comprises film forming saturated phospholipids.

9. The microvesicles of claim 6, wherein the phospholipids are selected from phosphatidic acid, phosphatidylcholine, phosphatidylethanolamine, phosphatidylserine, phosphatidylglycerol, phosphatidylinositol, cardiolipin and sphingomyelin.

10. The microvesicles of claim 9, wherein the phospholipids further contain substances selected from dicetylphosphate, cholesterol, ergosterol, phytosterol, sitosterol, lanosterol, tocopherol, propyl gallate, ascorbyl palmitate, butylated hydroxytoluene and fatty acids.

11. The microvesicles of claim 10, wherein the phospholipids comprise lecithins or derivative thereof.

12. The microvesicles of claim 1, comprising a fluorinated high molecular weight hydrocarbon gas, and stabilized by monolayers of said phospholipid material.

13. The microvesicles of claim 1 wherein said polymer is selected from natural or synthetic proteins, hydrocarbons, fluorinated hydrocarbons, polymerisable phospholipids and polyamino acids.

14. The microvesicles of claim 1 wherein the polymer is a biodegradable polymer selected from polysaccharides, polyamino-acids, polylactides and polyglycolides and their copolymers, copolymers of lactides and lactones, polypeptides, poly-(ortho)esters, polydioxanone, poly-β-aminoketones, polyphosphazenes, polyanhydrides and polyalkyl(cyano)acrylates.

15. The microvesicles of claims 1 wherein the membrane polymer is selected from polyglutamic or polyaspartic acid derivatives and their copolymers with other amino-acids.

16. An aqueous dispersion comprising the gas microvesicles of claim 6.

17. An aqueous dispersion comprising the gas microvesicles of claim 6 containing, dissolved, viscosity enhancers or stabilizers selected from linear and cross-linked poly- and oligo-saccharides, sugars, hydrophilic polymers and iodinated compounds in a weight ratio to the surfactants comprised between about 1:5 to 100:1.

18. The aqueous dispersion of claim 17, further comprising up to 50% by weight of non-laminar surfactants selected from fatty acids, esters of fatty acids and alcohols or polyols, and ethers of alcohols and/or polyols.

19. The aqueous dispersion of claim 18, wherein the polyols are polyalkylene glycols, polyalkylenated sugars and other carbohydrates, and polyalkylenated glycerol.

20. An aqueous dispersion of the gas microvesicles of claim 1, containing $10^7$–$10^8$, or $10^8$–$10^9$, or $10^{10}$–$10^{11}$ microbubbles/ml.

21. A process for preparation of an MRI contrast agent which comprises generating gas microvesicles containing a biocompatible hyperpolarized gas and a halogenated gas in a carrier liquid comprising one or more surfactants capable of generating gas-containing microvesicles.

22. The process of claim 21, which comprises shaking or sonicating a fluorinated and a hyperpolarized gas(es) in an amphiphile-containing liquid comprising a phospholipid.

23. The process of claim 21, wherein the contrast agent is isolated by freeze drying.

24. An MRI contrast agent prepared by the process of claim 21.

25. A diagnostic MRI contrast agent prepared according to claim 22 for use in MRI imaging of organs and tissue of human and animal patients.

26. A bifunctional MRI and ultrasonic contrast agent prepared according to the process of claim 22.

27. A kit comprising a dry formulation comprising a surfactant material capable of formation of gas-containing microvesicles of claim 1 under atmosphere of a mixture of a hyperpolarized gas and at least one biocompatible halogenated gas, and an aqueous carrier liquid.

28. A kit comprising a dry formulation comprising a surfactant material capable of formation of gas-containing microvesicles of claim 1, stored under partial pressure of the stabilising gas, a second component a hyperpolarized gas and a third component physiologically acceptable carrier liquid.

* * * * *